United States Patent
Gharda et al.

(10) Patent No.: US 10,202,352 B2
(45) Date of Patent: Feb. 12, 2019

(54) PROCESS FOR PREPARATION OF AMINOPYRAZOLE

(71) Applicant: GHARDA CHEMICALS LIMITED, Thane, Maharashtra (IN)

(72) Inventors: Keki Hormusji Gharda, Mumbai (IN); Laxminarayan Subraya Shet, Khed Taluka (IN); Yatin Shashikant Samangadkar, Khed Taluka (IN); Abhijeet Suresh Kawade, Khed Taluka (IN); Sachin Bhiku Jadhav, Khed Taluka (IN); Ashish Chandrakant Gogavale, Khed Taluka (IN)

(73) Assignee: GHARDA CHEMICALS LIMITED, Maharashtra (IN)

( * ) Notice: Subject to any disclaimer, the term of this patent is extended or adjusted under 35 U.S.C. 154(b) by 0 days.

(21) Appl. No.: 15/766,271

(22) PCT Filed: Sep. 20, 2016

(86) PCT No.: PCT/IB2016/055603
§ 371 (c)(1),
(2) Date: Apr. 5, 2018

(87) PCT Pub. No.: WO2017/060787
PCT Pub. Date: Apr. 13, 2017

(65) Prior Publication Data
US 2018/0282284 A1    Oct. 4, 2018

(30) Foreign Application Priority Data

Oct. 7, 2015    (IN) .......................... 3815/MUM/2015

(51) Int. Cl.
*C07D 231/38*    (2006.01)

(52) U.S. Cl.
CPC ................................... *C07D 231/38* (2013.01)

(58) Field of Classification Search
CPC ..................................................... C07D 231/38
See application file for complete search history.

(56) References Cited

U.S. PATENT DOCUMENTS

| 7,777,052 B2 | 8/2010 | Gharda et al. |
| 2009/0030211 A1 | 1/2009 | Gharda et al. |

FOREIGN PATENT DOCUMENTS

| EP | 0295117 A1 | 12/1988 |
| EP | 2069311 B1 | 5/2012 |

OTHER PUBLICATIONS

International Search Report for PCT/IB2016/055602, ISA/IN, Dwarka, New Delhi, dated Dec. 22, 2016.
Written Opinion of the ISA for PCT/IB2016/055602, ISA/IN, Dwarka, New Delhi, dated Dec. 22, 2016.

*Primary Examiner* — Joseph R Kosack
(74) *Attorney, Agent, or Firm* — Harness, Dickey & Pierce, P.L.C.

(57) ABSTRACT

The present disclosure relates to an improved diazotization process for the preparation of 5-amino-3-cyano-1-(2,6-dichloro-4-trifluoromethylphenyl) pyrazole.

14 Claims, No Drawings

PROCESS FOR PREPARATION OF AMINOPYRAZOLE

FIELD

The present disclosure relates to a process for preparing aminopyrazole, particularly 5-amino-3-cyano-1-(2,6-dichloro-4-trifluoromethylphenyl)pyrazole.

Definitions

As used in the present disclosure, the following words and phrases are generally intended to have the meaning as set forth below, except to the extent that the context in which they are used indicate otherwise.

The expression 'Spent acid' for the purpose of the present disclosure refers to waste HCl and waste $H_2SO_4$ generated during trichloromethanesulfenyl chloride synthesis, or during thiophosgene synthesis.

BACKGROUND

Some compounds of the aryl pyrazole family are known to possess excellent insecticidal activity. Within this family of compounds, Fipronil, 5-amino-3-cyano-1-(2,6-dichloro-4-trifluoromethylphenyl)-4-trifluoromethylsulfinylpyrazole, has potent activity against insects and acarids. Fipronil binds to the gamma aminobutyric acid (GABA) receptors in the cell membranes of invertebrate neurons, functionally stabilizing the closed form of the channel, resulting in death of invertebrates. Fipronil has a chemical structure as shown herein below, as structure I:

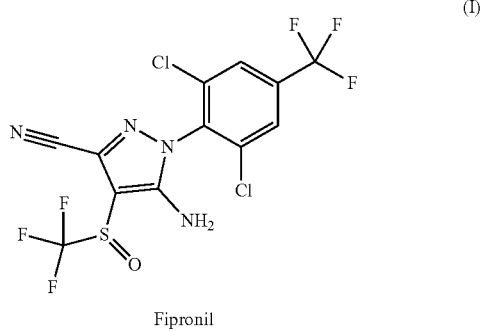 [SMILES: N#Cc1nn(-c2c(Cl)cc(C(F)(F)F)cc2Cl)c(N)c1S(=O)C(F)(F)F]

Fipronil 5-amino-3-cyano-1-(2,6-dichloro-4-trifluoromethylphenyl)pyrazole is an important intermediate used in the process for preparation of Fipronil and has the following chemical structure shown herein below, as structure (II):

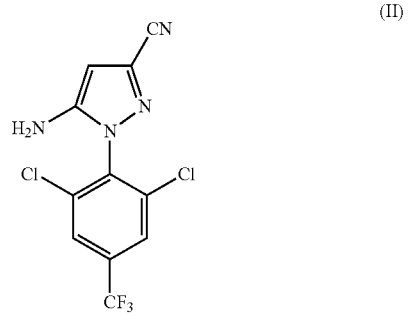 [SMILES: N#Cc1cc(N)n(-c2c(Cl)cc(C(F)(F)F)cc2Cl)n1]

Various synthetic routes are available for the preparation of aminopyrazole i.e., 5-amino-3-cyano-1-(2,6-dichloro-4-trifluoromethylphenyl)pyrazole.

These synthetic routes are accompanied with various drawbacks such as generation of large amounts of acidic effluent, several reaction steps, and difficulty in dealing with the waste acid, use of toxic reagents, low purity, and low yield of product. Therefore, there is a need for a simple process having minimum process steps, superior product quality, reasonable cost, and excellent synthetic route to achieve large-scale industrial production and which is environment friendly.

Thus, there is felt need for a process for preparing 5-amino-3-cyano-1-(2,6-dichloro-4-trifluoromethylphenyl) pyrazole (intermediate of Fipronil) in high yield in a simple, economical and environment friendly manner.

OBJECTS

Some of the objects of the present disclosure, which at least one embodiment herein satisfies, are as follows.

It is an object of the present disclosure to ameliorate one or more problems of the prior art or to at least provide a useful alternative.

An object of the present disclosure is to provide a process for the preparation of aminopyrazole Another object of the present disclosure is to provide a process for the preparation of 5-amino-3-cyano-1-(2,6-dichloro-4-trifluoromethylphenyl)pyrazole.

Still another object of the present disclosure is to provide a process which is simple economic and environment friendly.

Yet another object of the present disclosure is to provide a process for the preparation of aminopyrazole that gives high yield and high purity.

Other objects and advantages of the present disclosure will be more apparent from the following description, which is not intended to limit the scope of the present disclosure.

SUMMARY

The present disclosure provides a process for the preparation of aminopyrazole. The aminopyrazole is particularly, 5-amino-3-cyano-1-(2,6-dichloro-4-trifluoromethylphenyl) pyrazole. The process steps involve the step of reacting 2,6 dichloro-4-trifluoromethylaniline (DCTFMA) with a mixture of spent HCl and spent $H_2SO_4$ in at least one fluid medium and in at least one wetting agent to obtain a slurry comprising the salts of 2,6-dichloro-4-trifluoromethyl aniline. To the slurry, $NaNO_2$ solution is added for diazotizing the salts of 2,6-dichloro-4-trifluoromethyl aniline, over a period of 30 minutes to 180 minutes under stirring at a temperature in the range of 15° C. to 25° C. to obtain a suspension comprising diazotized salt of 2,6-dichloro-4-trifluoromethylaniline followed by diluting it with water to obtain a mixture. A dicyanopropionic acid ester is added to the mixture while stirring it for 10 hours to 12 hours to obtain a biphasic system. The organic phase is separated from the biphasic system and the separated organic phase is treated with an aqueous alkali solution and cooled to a temperature in the range of 8° C. to 10° C. to obtain a precipitate comprising aminopyrazole compound. The so obtained precipitate is filtered to obtain a cake, which is washed with water and dried it under vacuum to obtain aminopyrazole.

DETAILED DESCRIPTION

The disclosure will now be described with reference to the accompanying embodiments which do not limit the scope and ambit of the disclosure. The description provided is purely by way of example and illustration.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The following description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein has been described in terms of preferred embodiments, those skilled in the art will recognize that the embodiments herein can be practiced with modification within the spirit and scope of the embodiments as described herein.

Conventionally, the process for preparation of 5-amino-3-cyano-1-(2,6-dichloro-4-trifluoromethylphenyl)pyrazole, produces hazardous waste and provides a product having low purity along with low yield.

5-amino-3-cyano-1-(2,6-dichloro-4-trifluoromethylphenyl)pyrazole herein referred to as aminopyrazole has a chemical structure as shown below;

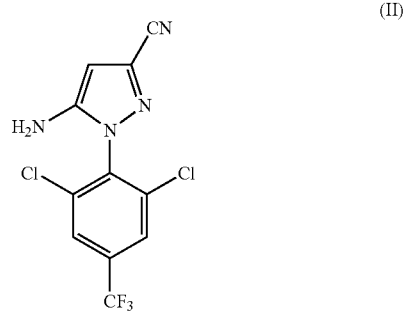 [SMILES: N#Cc1cc(N)n(-c2c(Cl)cc(C(F)(F)F)cc2Cl)n1]

(II)

To ameliorate one or more of the above mentioned problems, the present disclosure envisages a process for the preparation of aminopyrazole, wherein the step of diazotization is carried out by using a mixture of spent acids. Further, the process of the present disclosure uses less toxic reagents and produces a compound having high purity and high yield.

In accordance with the present disclosure there is provided a process for preparing aminopyrazole. The process is described herein below:

Step (a):

In step (a), 2,6 dichloro-4-trifluoromethylaniline (DCTFMA) is reacted with a mixture of spent HCl and spent $H_2SO_4$ in at least one fluid medium and in at least one wetting agent to obtain a slurry comprising the salts of 2,6-dichloro-4-trifluoromethyl aniline.

The fluid medium can be dichloromethane, dichloroethane, toluene, alcohol, chlorobenzene and the like. The amount of fluid medium used in step (a) of the process ranges from 50 ml to 400 ml per mole of DCTFMA.

The wetting agent is can be selected from the group that includes, but is not limited to, non-ionic surfactants such as nonylphenol ethoxylate (NP-10), sucrose polyestearate (SP-10), and the like. The amount of wetting agent used in step (a) ranges from 0.2 g/mole to 1 g/mole of DCTFMA. The wetting agent maintains the mixture in a homogeneous form. Due to the presence of the wetting agent, the DCTFMA salt formed in the process of the present disclosure remains as a homogenous slurry, without any hard solidification or adhering to the walls. If the DCTFMA salt adheres to the walls of the reactor/vessel, the yield and purity of aminopyrazole are affected.

In existing methods, the diazotization process of 2,6-dichloro-4-trifluoromethylaniline (DCTFMA) is carried out by using 24 wt % to 35 wt % of nitrosyl sulfate solution. The process of diazotization generates 20-22 w/w % of spent $H_2SO_4$ & its disposal is a major issue and also costly. Further, a mixture of $HCl+H_2SO_4$ is generated in large quantities via chlorination of $CS_2$ to $CCl_3SCl$ during Fipronil synthesis. The process of disposal of the mixture of so obtained waste HCl and waste $H_2SO_4$ (spent HCl and spent $H_2SO_4$) obtained from the chlorination process is costly and is harmful to the environment. Also, neutralization of these acids consumes a large amount of caustic, which also needs to be disposed.

Hence, the inventors of the present disclosure have developed a process for diazotization of 2,6-dichloro-4-trifluoromethylaniline using $NaNO_2$ (Sodium nitrite) and the mixture of spent HCl and spent $H_2SO_4$, without the use of reagents such as nitrosyl sulfate.

In an embodiment of the present disclosure, the process starts with mixing a fluid medium, at least one wetting agent and 2,6 dichloro-4-trifluoromethylaniline (DCTFMA) to obtain a mixture. A mixture of spent HCl and spent $H_2SO_4$ is added in the mixture to obtain a slurry containing salts of 2,6-dichloro-4-trifluoromethyl aniline.

The addition of a mixture of acids into the mixture is carried out at 25° C. to 60° C. for 1 hour to 3 hours. The amount of spent HCl and spent $H_2SO_4$ mixture used in the process of the present disclosure ranges from 0.5 liters to 2 liters per mole of DCTFMA. The molar ratio of HCl to $H_2SO_4$ used in the mixture ranges from 9:2 to 10:2 The so obtained salts are hydrochloride salts of 2,6-dichloro-4-trifluoromethylaniline and sulfate salts of 2,6-dichloro-4-trifluoromethylaniline. The salts are in the form of a homogeneous slurry due to the presence of the wetting agent.

Step (b):

In step (b) of the process, the homogenous slurry obtained in step (a) is kept under stirring for 1 hour at 15° C. to 25° C. and diazotized by adding $NaNO_2$ solution to the slurry. Sodium nitrite ($NaNO_2$) solution is obtained by dissolving $NaNO_2$ in water. The amount of sodium nitrite can range from 0.9 g mole to 1.20 g mole. The addition of $NaNO_2$ solution in the homogenous slurry is carried out in the temperature range of 15° C. to 30° C. for a time period ranging from 30 minutes to 4 hours. The reaction is further stirred for 1 hour to obtain a clear solution comprising diazotized salt.

In one embodiment the diazotized salt is hydrochloride salt 2,6-dichloro-4-trifluoromethylaniline and sulfate salt of 2,6-dichloro-4-trifluoromethylaniline.

Step (c):

The so obtained clear solution is poured into ice cold water and further maintained under stirring for 1 hour to obtain a mixture. The mixture comprises a diazo mass of hydrochloride and sulfate salts which get dissolved in ice cold water. The process of stirring is maintained throughout the reaction.

Step (d):

In step (d) of the process of the present disclosure, at least one dicyanopropionic acid ester is gradually added into the mixture at a temperature in the range of 20° C. to 30° C. for a time period ranging from 25 minutes to 35 minutes. After complete addition of dicyanopropionic acid ester, the stirring of the reaction is further maintained for a time period ranging from 10 hours to 12 hours to obtain a biphasic system comprising the coupled product.

Dicyanopropionic acid ester can be selected from the group that includes, but is not limited to, dicyanopropionic acid methyl ester, dicyanopropionic acid ethyl ester, dicyanopropionic acid propyl ester and dicyanopropionic acid butyl ester.

Step (e):

In step (e), the organic phase is separated from the so obtained biphasic system. The aqueous phase is washed with toluene and toluene layer is separated. The separated toluene layer is mixed with separated organic phase and reacted with at least one alkaline solution at a temperature in the range of 10° C. to 25° C. The alkaline solution can be sodium hydroxide (NaOH), sodium carbonate ($Na_2CO_3$), potassium carbonate ($K_2CO_3$) and potassium hydroxide (KOH) solution. The concentration of alkaline solution is in the range from 1 M to 2 M.

Upon completion of the above step, the reaction mass is further stirred at a temperature in the range of 25° C. to 40° C. for a time period ranging from 30 minutes to 2 hours to obtain a product precipitate.

Step (f):

In step (f), the so obtained precipitate is cooled to a temperature ranging from 8° C. to 10° C. and is filtered to obtain a cake. The filtered cake is washed with water to make it free of alkalinity and dried under vacuum to obtain the aminopyrazole compound of structure II.

In one embodiment, the aminopyrazole obtained from the process of the present disclosure is 5-amino-3-cyano-1-(2, 6-dichloro-4-trifluoromethylphenyl) pyrazole.

The process of the present disclosure for preparation of aminopyrazole is economical and environment friendly, as the step of diazotization uses a mixture of spent HCl and Spent $H_2SO_4$ and $NaNO_2$ to obtain 80% to 92% yield of the product and the purity of the product is at least 99% by HPLC.

The present disclosure is further illustrated herein below with the help of the following experiments. The experiments used herein are intended merely to facilitate an understanding of ways in which the embodiments herein may be practiced and to further enable those of skill in the art to practice the embodiments herein. Accordingly, the examples should not be construed as limiting the scope of embodiments herein. These laboratory scale experiments can be scaled up to an industrial/commercial scale.

Experimental Details

Experiment 1

Process of preparation of 5-amino-3-cyano-1-(2,6-dichloro-4-trifluoromethyl phenyl)pyrazole in accordance with present disclosure A 4-Neck 2.0 liter capacity glass reactor with an overhead stirrer system was set for the reaction. 150 ml of toluene was added to the reactor. 0.5 gm of sucrose polystearate (SP-20) & 230 gm of 2,6-dichloro-4-trifluoromethylaniline was added to the reactor under stirring.

To this solution, 600 ml 13.9 N spent acid solution having 3.9N sulfuric acid and 10 N HCl was gradually added over 30 minutes at 30° C. to 40° C. The reaction mixture comprised a mixture of 2,6-dichloro-4-trifluoromethylaniline salts, which was stirred for 1 hour at 30 to 40° C. and then cooled to 15° C. to 20° C.

75.9 gm sodium nitrite was dissolved in 100 ml $H_2O$ to get sodium nitrite solution. This sodium nitrite solution was added into the reaction mixture comprising a mixture of 2,6-dichloro-4-trifluoromethylaniline salts, over a period of 3 hours at 15° C. to 20° C. The reaction mixture containing diazotized salt was stirred for 1 hour at 15° C. to 20° C. After 1 hour, the reaction mixture was poured into 1200 gm chilled ice water while controlling temperature below 20° C.

To this diluted diazo mass at 10° C. to 15° C., 152 gm of 2,3-dicyanopropionic acid ethyl ester was added with stirring over 30 minutes by maintaining the temperature at 10° C. to 15° C. Stirring was continued for 12 hours at 15° C. to 25° C. to get a biphasic system containing coupled product. After 12 hours, stirring of the reaction mixture was stopped. The organic layer was separated as coupled product and the aqueous layer was extracted with 100 ml toluene. The extracted toluene layer was mixed with the organic layer comprising the cyclized product. The coupled product solution was added into 1000 ml, 2 N sodium hydroxide solutions at temperature 5° C. to 25° C. and stirred for 4 hours at 20° C. to 25° C.

The organic phase after addition of sodium hydroxide was further heated to 40° C. to 42° C. and equilibrated for 1 hour.

The precipitated product slurry was cooled back to 10° C. to 15° C. and filtered. The filtered cake was washed with water to make it free of alkalinity followed by 50 ml of chilled toluene wash. The isolated product is 5-amino-3-cyano-1-(2,6-dichloro-4-trifluoromethylphenyepyrazole (structure II) having 80% yield with 99.0% HPLC purity.

Experiment 2-13

Process of preparation of 5-amino-3-cyano-1-(2,6-dichloro-4-trifluoromethyl phenyl)pyrazole in accordance with present disclosure Similar experiments were carried out (expt 2-13) by varying the normality of spent HCl and spent $H_2SO_4$ and mixtures thereof, and by varying the reaction conditions. The results obtained from the process of the present disclosure by such variations are summarized in table 1.

TABLE 1

| Exp no | Normality of mixture of spent acids | Normality of Spent H2SO4 | Normality of Spent HCl | Reaction condition | Addition of dicynopropionic acid ester for cyclization | Ice cold water after neutralization | Purity of product by HPLC | yield of 5-amino-3-cyano-1-(2,6-dichloro-4-trifluoromethyl phenyl)pyrazole |
|---|---|---|---|---|---|---|---|---|
| 1 | 600 ml, 13.9N | 3.9N | 10N | 30 to 40 Deg C. over 30 min | 152 gm | 1200 gm | 99.00% | 80% |
| 2 | 700 ml, 14.1N | 4.1N | 10N | 30 to 60 Deg C. over 30 min | 152 gm | 1400 gm | 99.20% | 80% |
| 3 | 800 ml, 14.1N | 4.2N | 9.9N | 30 to 60 Deg C. over 30 min | 152 gm | 1600 gm | 99% | 84% |
| 4 | 800 ml, 14N | 4.2N | 9.8N | 30 to 40 Deg C. over 30 min | 152 gm | 1800 gm | 99% | 86% |
| 5 | 1000 ml, 14N | 4.4N | 9.8N | 30 to 40 Deg C. over 30 min | 152 gm | 1500 gm | 99.20% | 84% |
| 6 | 1000 ml, 14N | 4.2N | 9.8N | 30 to 40 Deg C. over 30 min | 152 gm | 2000 gm | 99.50% | 89% |
| 7 | 1000 ml, 14.2N | 4.3N | 9.9N | 30 to 50 Deg C. over 30 min | 152 gm | 2500 gm | 99% | 90% |
| 8 | 1200 ml, 14.2N | 4.4N | 9.8N | 30 to 40 Deg C. over 30 min | 152 gm | 2500 gm | 99.10% | 91% |
| 9 | 1000 ml, 14.1N | 4.2N | 9.9N | 30 to 40 Deg C. over 30 min | 138 gm | 2000 gm | 99.50% | 90% |
| 10 | 1000 ml, 14.1N | 4.1N | 9.9N | 30 to 40 Deg C. over 30 min | 152 gm | 2000 gm | 99.50% | 85% |
| 11 | 1000 ml, 14.1N | 4.1N | 10N | 30 to 40 Deg C. over 30 min | 138 gm | 2000 gm | 99.20% | 89% |
| 12 | 1000 ml, 14.3N | 4.4N | 9.9N | 30 to 40 Deg C. over 30 min | 138 gm | 2000 gm | 99.30% | 86% |
| 13 | 1000 ml, 14.3N | 4.4N | 9.9N | 30 to 40 Deg C. over 30 min | 152 gm | 2000 gm | 99.20% | 85% |

From experiments 1-13, it is observed that the process gives high purity and high yield of aminopyrazole (5-amino-3-cyano-1-(2,6-dichloro-4-trifluoromethyl phenyl)pyrazole), despite using spent acids and the effluent obtained from the process does not need to be neutralized further.

Experiment No. 14 (Reverse Addition)

Process of preparation of 5-amino-3-cyano-1-(2,6-dichloro-4-trifluoromethyl phenyl)pyrazole in accordance with present disclosure A 4-Neck 2.0 liter capacity glass reactor with an overhead stirrer system was set for the reaction. 1000 ml of spent acid solution having 10.0 N HCl & 4.0 N H$_2$SO$_4$ was taken into the reactor. 0.2 gm of sucrose polystearate (SP-20) was added to the spent acid solution into the reactor. To this solution, 230 gm 2,6-dichloro-4-trifluoromethylaniline and 300 ml toluene (mixture of aniline and toluene) was added over 1.0 hour at 30 to 50° C. The reaction mixture comprised a mixture of 2,6-dichloro-4-trifluoromethylaniline salts, which was stirred for 1 hour at 30 to 50° C. and then cooled to 15° C. to 20° C.

75.9 gm sodium nitrite was dissolved in 100 ml H$_2$O to get sodium nitrite solution. This sodium nitrite solution was added into reaction mixture comprising a mixture of 2,6-dichloro-4-trifluoromethylaniline salts, over a period of 3 hours at 15° C. to 20° C. The reaction mixture containing diazotized salt was stirred for 1 hour at 15° C. to 20° C. After 1 hour, the reaction mixture was poured into 2000 gm chilled ice water while controlling the temperature below 20° C. To this diluted diazo mass at 10° C. to 15° C., 152 gm of 2,3-dicyanopropionic acid methyl ester was added with stirring over 30 minutes by maintaining the temperature at 10° C. to 15° C. Stirring was continued for 12 hours at 15° C. to 25° C. to get a biphasic system containing cyclized product. After 12 hours, stirring of the reaction mixture was stopped. The organic layer was separated as a coupled product and the aqueous layer was extracted with 100 ml toluene. The extracted toluene layer was mixed with the organic layer comprising the coupled product. The coupled product solution was added into 1000 ml, 2 N sodium hydroxide solutions at temperature 5° C. to 25° C. and stirred for 4 hours at 20° C. to 25° C.

The organic phase after addition of sodium hydroxide was further heated to 40° C. to 42° C. and equilibrated for 1 hour.

The precipitated product slurry was cooled back to 10° C. to 15° C. and filtered. The filtered cake was washed with water to make it free of alkalinity followed by 50 ml of chilled toluene wash. The isolated product is 5-amino-3-cyano-1-(2,6-dichloro-4-trifluoromethylphenye)pyrazole (structure II) having 85% yield with 99.0% HPLC purity. From the above experiment, it is observed that changing the sequence of addition of the reactants of step (a) does not affect the purity and yield of 5-amino-3-cyano-1-(2,6-dichloro-4-trifluoromethylphenyl)pyrazole (structure II).

Technical Advances and Economical Significance

The present disclosure described herein above has several technical advantages including, but not limited to, the realization of a process that provides 85-92% yield of 5-amino-3-cyano-1-(2,6-dichloro-4-trifluoromethylphenyl)pyrazole (aminopyrazole);

is cost effective, simple and environment friendly;

requires no disposal cost; and no purification is required for aminopyrazole.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the disclosure to achieve one or more of the desired objects or results.

Any discussion of documents, acts, materials, devices, articles or the like that has been included in this specification is solely for the purpose of providing a context for the disclosure. It is not to be taken as an admission that any or all of these matters form a part of the prior art base or were common general knowledge in the field relevant to the disclosure as it existed anywhere before the priority date of this application.

The numerical values mentioned for the various physical parameters, dimensions or quantities are only approximations and it is envisaged that the values higher/lower than the numerical values assigned to the parameters, dimensions or quantities fall within the scope of the disclosure, unless there is a statement in the specification specific to the contrary.

While considerable emphasis has been placed herein on the components and component parts of the preferred embodiments, it will be appreciated that many embodiments can be made and that many changes can be made in the preferred embodiments without departing from the principles of the disclosure. These and other changes in the preferred embodiment as well as other embodiments of the disclosure will be apparent to those skilled in the art from the disclosure herein, whereby it is to be distinctly understood that the foregoing descriptive matter is to be interpreted merely as illustrative of the disclosure and not as a limitation.

The invention claimed is:

1. A process for preparing aminopyrazole, said process comprising the following steps:
   a. reacting dichloro trifluoromethyl aniline with an acidic mixture of spent HCl and spent $H_2SO_4$ in at least one fluid medium and in at least one wetting agent to obtain a slurry comprising a mixture of chloride salt and sulfate salt of dichloro trifluoromethyl aniline;
   b. diazotizing said salts from step (a) by reacting said slurry with aqueous sodium nitrite ($NaNO_2$) to obtain a diazotized salt of dichloro trifluoromethyl aniline;
   c. diluting said diazotized salt with water to obtain a mixture;
   d. adding at least one dicyanopropionic acid ester to said mixture while stirring for a time period ranging from 10 hours to 12 hours to obtain a biphasic system comprising an organic phase and an aqueous phase;
   e. separating the components of said biphasic system to obtain an organic phase and treating said organic phase with at least one aqueous alkali solution and cooling it to a temperature in the range of 8° C. to 10° C. to obtain a precipitate comprising an aminopyrazole compound; and
   f. filtering said precipitate to obtain a residue and washing said residue with water, followed by drying under reduced pressure to obtain the aminopyrazole.

2. The process as claimed in claim 1, wherein said aminopyrazole is 5-amino-3-cyano-1-(2,6-dichloro-4-trifluoromethylphenyl)pyrazole.

3. The process as claimed in claim 1, wherein said dichloro trifluoromethyl aniline is 2,6-dichloro-4-trifluoromethyl aniline.

4. The process as claimed in claim 1, wherein said fluid medium is at least one selected from the group consisting of dichloromethane, dichloroethane, toluene, chlorobenzene, bromobenzene and $C_1$-$C_6$ alcohols.

5. The process as claimed in claim 1, wherein said wetting agent is at least one non-ionic surfactant.

6. The process as claimed in claim 5, wherein said non-ionic surfactant is selected from the group consisting of sucrose polystearate and nonylphenol ethoxylate.

7. The process as claimed in claim 1, wherein the amount of said mixture of spent HCl and spent $H_2SO_4$ ranges from 0.5 liters to 2 liters per mole of dichloro trifluoromethyl aniline.

8. The process as claimed in claim 1, wherein the molar ratio of HCl to $H_2SO_4$ in said mixture ranges from 9:2 to 10:2.

9. The process as claimed in claim 1, wherein the amount of said sodium nitrite ranges from 0.9 g mole to 1.20 g mole.

10. The process as claimed in claim 1, wherein said dicyanopropionic acid ester is at least one selected from the group consisting of dicyanopropionic acid methyl ester, dicyanopropionic acid ethyl ester, dicyanopropionic acid propyl ester, and dicyanopropionic acid butyl ester.

11. The process as claimed in claim 1, wherein said step (a) of reacting a mixture of spent HCl and spent $H_2SO_4$ with dichloro trifluoromethyl aniline is carried out at a temperature in the range of 25° C. to 40° C. over a time period in the range of 60 minutes to 180 minutes.

12. The process as claimed in claim 1, wherein said sodium nitrite is added to the reaction mixture over a time period ranging from 30 minutes to 180 minutes at a temperature ranging from 15° C. to 30° C.

13. The process as claimed in claim 1, wherein said aqueous alkali in step (e) is at least one selected from a group consisting of NaOH, KOH, $Na_2CO_3$, and $K_2CO_3$.

14. The process as claimed in claim 1, wherein said aminopyrazole has a purity of at least 98% and said process has a yield of at least 80%.

* * * * *